United States Patent [19]

Satoh et al.

[11] Patent Number: 5,256,794

[45] Date of Patent: Oct. 26, 1993

[54] SQUARYLIUM COMPOUNDS

[75] Inventors: Tsutomu Satoh, Yokohama; Ikuo Shimizu; Yukiyoshi Ito, both of Yokkaichi, all of Japan

[73] Assignees: Ricoh Company, Ltd.; Kyowa Hakko Kogyo Co. Ltd., both of Tokyo, Japan

[21] Appl. No.: 550,309

[22] Filed: Jul. 9, 1990

[30] Foreign Application Priority Data

Dec. 7, 1989 [JP] Japan .................................. 1-179631

[51] Int. Cl.$^5$ ............................................ C07D 209/12
[52] U.S. Cl. ...................................... 548/491; 548/490
[58] Field of Search ................................ 548/490, 491

[56] References Cited

FOREIGN PATENT DOCUMENTS

| | | |
|---|---|---|
| 0278441 | 8/1988 | European Pat. Off. |
| 0295144 | 12/1988 | European Pat. Off. |
| 0305054 | 3/1989 | European Pat. Off. |
| 0218616 | 2/1910 | Fed. Rep. of Germany ...... 548/491 |
| 1063302 | 3/1967 | United Kingdom ............... 548/491 |

*Primary Examiner*—David B. Springer
*Attorney, Agent, or Firm*—Cooper & Dunham

[57] ABSTRACT

Squarylium compounds having the following formula (I),

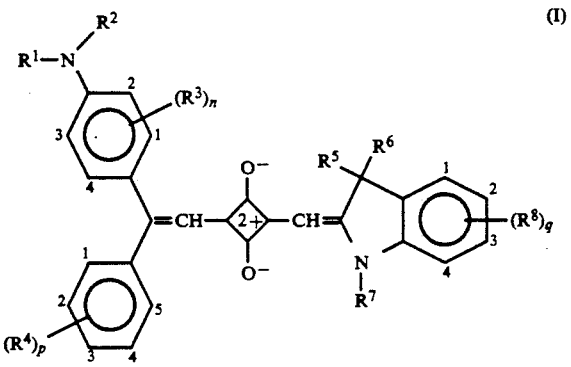

and an optical information recording medium comprising a substrate and a recording layer formed on the substrate, comprising a squarylium compound having formula (I) are disclosed.

8 Claims, 7 Drawing Sheets

SQUARYLIUM COMPOUNDS

BACKGROUND OF THE INVENTION

1. Field of the Invention

This invention relates to squarylium compounds which absorb near infrared rays, and to an optical information recording medium using the squarylium compounds.

2. Discussion of Background

Materials capable of absorbing near infrared rays have various uses, for example, for (i) safe-light filters for photosensitive materials which are sensitive to infrared rays; (ii) infrared filters for controlling the growth of plants; (iii) materials for intercepting the heat rays in sunlight (iv) infrared filters for protecting eye tissues from infrared rays; and (v) infrared filters for the light receiving elements of semiconductors.

In addition to the above, a recording material of an optical information recording medium is one of the important applications of the above-mentioned near-infrared-ray-absorbing materials.

Conventionally, cyanine dyes such as phthalocyanine dyes; phenanthrene dyes; naphthoquinone dyes; and pyrylium dyes are known as materials capable of absorbing near infrared rays. In Japanese Laid-Open Patent Applications 55-97033, 58-83344, 58-224793, 58-214162 and 59-24692, optical information recording media are disclosed which comprise the aforementioned dyes as recording materials.

Each of the above-mentioned dyes, however, has its own shortcomings. More specifically, phthalocyanine dyes are disadvantageous in that they have low photosensitivity and high decomposition point, and are not readily vacuum-deposited. In addition, since they have extremely low solubility in organic solvents, they cannot be applied by liquid coating.

Phenanthrene dyes and naphthoquinone dyes ar readily vacuum-deposited, but low in reflectance. The low reflectance causes a low contrast between one portion in which information is recorded by application of laser beads and the other portion in which no information is recorded. This will bring about inaccurate reproduction of the recorded information.

Pyrylium dyes and cyanine dyes are soluble in solvents, so that they can be applied by liquid coating. However, these dyes are so poor in light-resistance that they are readily deteriorated when exposed to the light employed for the reproduction of recorded information.

SUMMARY OF THE INVENTION

Accordingly, one object of this invention is to provide squarylium compounds capable of highly absorbing near infrared rays, which are easily vacuum-deposited, and have high solubility in organic solvents, high preservation stability and high light resistance.

Another object of the present invention is to provide an optical information recording medium comprising such compounds, which recording medium shows a sharp contrast between a recorded area and a non-recorded area, with high reflectance, and has improved preservation stability and stability to the light employed for the reproduction of recorded information.

The first object of the present invention can be achieved by squarylium compounds having formula (I):

(I)

in which $R^1$ and $R^2$ independently represent hydrogen, an alkyl group having 1 to 4 carbon atoms, an aryl group which may have a substituent, or an aralkyl group having 7 to 10 carbon atoms, which may have a substituent;

$R^3$ represents a halogen, an alkyl group having 1 to 4 carbon atoms, an alkoxyl group having 1 to 4 carbon atoms, a nitro group, or a hydroxyl group; n is an integer of 0 to 4 and $R^3$s may be the same or different when n is 2 to 4;

$R^4$ represents a halogen, an alkyl group having 1 to 4 carbon atoms, an alkoxyl group having 1 to 4 carbon atoms, a hydroxyl group, a nitro group, a cyano group, a trifluoromethyl group, or $$-N\begin{matrix}R^9\\R^{10}\end{matrix}$$

in which $R^9$ and $R^{10}$ are the same defined in $R^1$; p is an integer of 0 to 5 and $R^4$s may be the same or different when P is 2 to 5;

$R^5$ and $R^6$ independently represent an alkyl group having 1 to 4 carbon atoms;

$R^7$ represents an alkyl group having 1 to 4 carbon atoms, an aryl group which may have a substituent, or an aralkyl group having 7 to 10 carbon atoms, which may have a substituent;

$R^8$ represents a halogen, an alkyl group having 1 to 4 carbon atoms, an alkoxyl group having 1 to 4 carbon atoms, an aryl group which may have a substituent, or an aralkyl group having 7 to 10 carbon atoms, which may have a substituent; and q is an integer of 0 to 4 and when q is 2 to 4, $R^8$s may be the same or different and form an aromatic ring which may have a substituent, in combination with two adjacent carbon atoms in the ring to which $R^8$s are bonded.

The second object of the present invention can be achieved by an optical information recording medium which comprises a substrate and a recording layer formed on the substrate, which comprises the above-mentioned squarylium compounds of formula (I).

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

The squarylium compounds according to the present invention are represented by the following formula (I):

in which $R^1$ and $R^2$ independently represent hydrogen, an alkyl group having 1 to 4 carbon atoms, an aryl group which may have a substituent, or an aralkyl group having 7 to 10 carbon atoms, which may have a substituent;

$R^3$ represents a halogen, an alkyl group having 1 to 4 carbon atoms, an alkoxyl group having 1 to 4 carbon atoms, a nitro group, or a hydroxyl group; n is an integer of 0 to 4 and $R^3$s may be the same or different when n is 2 to 4;

$R^4$ represents a halogen, an alkyl group having 1 to 4 carbon atoms, an alkoxyl group having 1 to 4 carbon atoms, a hydroxyl group, a nitro group, a cyano group, a trifluoromethyl group, or in which $R^9$ and $R^{10}$ are the same as defined in $R^1$; p is an integer of 0 to 5 and $R^4$s may be the same or different when p is 2 to 5;

$R^5$ and $R^6$ independently represent an alkyl group having 1 to 4 carbon atoms;

$R^7$ represents an alkyl group having 1 to 4 carbon atoms, an aryl group which may have a substituent, or an aralkyl group having 7 to 10 carbon atoms, which may have a substituent;

$R^8$ represents a halogen, an alkyl group having 1 to 4 carbon atoms, an alkoxyl group having 1 to 4 carbon atoms, an aryl group which may have a substituent, or an aralkyl group having 7 to 10 carbon atoms, which may have a substituent; and q is an integer of 0 to 4 and when q is 2 to 4, $R^8$s may be the same or different and may form an aromatic ring which may have a substituent, in combination with two adjacent carbon atoms in the ring to which $R^8$s are bonded.

In the above formula (I), specific examples of the alkyl group having 1 to 4 carbon atoms, represented by $R^1$, $R^2$, $R^3$, $R^4$, $R^5$, $R^6$, $R^7$, $R^8$, $R^9$ or $R^{10}$, include a methyl group, an ethyl group, a propyl group, an isopropyl group, a butyl group, an isobutyl group, a sec-butyl group and a tert-butyl group.

Examples of the alkoxyl group having 1 to 4 carbon atoms, represented by $R^3$, $R^4$ or $R^8$, are a methoxy group, an ethoxy group, a propoxy group and a butoxy group.

Examples of the halogen represented by $R^3$, $R^4$ or $R^8$ are chlorine, bromine and fluorine.

Examples of the aryl group represented by $R^1$, $R^2$, $R^7$, $R^8$, $R^9$ or $R^{10}$ include a phenyl group and a naphthyl group.

Examples of the aralkyl group having 7 to 10 carbon atoms, represented by $R^1$, $R^2$, $R^7$, $R^8$, $R^9$ or $R^{10}$, are a benzyl group, a phenylethyl group and phenylpropyl group.

Examples of the substituents of the aryl group and aralkyl group represented by $R^1$, $R^2$, $R^7$, $R^8$, $R^9$ or $R^{10}$ are a halogen such as chlorine, bromine and fluorine; an alkyl group having 1 to 4 carbon atoms, such as a methyl group, an ethyl group, a propyl group, an isopropyl group, a butyl group, an isobutyl group, a sec-butyl group and a tert-butyl group; and an alkoxyl group having 1 to 4 carbon atoms, such as a methoxy group, an ethoxy group, a propoxy group and a butoxy group.

An example of the aromatic ring in the definition of $R^8$ is a benzene ring.

Examples of the substituents of the aromatic ring formed by $R^8$s are a halogen such as chlorine, bromine and fluorine; an alkyl group having 1 to 4 carbon atoms, such as a methyl group, an ethyl group, a propyl group, an isopropyl group, a butyl group, an isobutyl group, a sec-butyl group and a tert-butyl group; an alkoxyl group having 1 to 4 carbon atoms, such as a methoxy group, an ethoxy group, a propoxy group and a butoxy group; an aralkyl group having 7 to 10 carbon atoms, such as a benzyl group, a phenylethyl group and a phenylpropyl group; and an aryl group such as a phenyl group and a naphthyl group.

The squarylium compounds according to the present invention can be prepared as follows:

3,4-dichloro-3-cyclobutene-1,2-dione is allowed to react with a 1,1-diarylethylene compound in a solvent. After the completion of the reaction, the solvent is distilled away from the reaction solution and a residue is hydrolyzed. The resultant product is then allowed to react with an indoline or indolium compound in a solvent while heating the reaction system, thereby preparing the desired squarylium compound. When an indolium compound is employed, the reaction is carried out in the presence of quinoline.

The scheme of the above reaction is as follows:

[Reaction Formula 1]

[Reaction Formula 2]

[Reaction Formula 3-a]

[Reaction Formula 3-b]

More specifically, in Reaction Formula 1, equimolar amounts of 3,4-dichloro-3-cyclobutene-1,2-dione [Compound (II)] and a 1,1-diarylethylene compound [Compound (III)] are allowed to react at room temperature in a solvent which is capable of dissolving the above two compounds therein and does not interrupt the reaction. The reaction is completed in 5 to 60 minutes. Examples of the above-mentioned solvent used in Reaction Formula 1 are chloroform, dichloromethane, 1,2-dichloromethane, diethyl ether, tetrahydrofuran, toluene, benzene, dimethylformamide and dimethyl sulfoxide. The solvent is distilled away from the reaction solution, whereby a crude product of Compound (IV) is obtained.

In Reaction Formula 2, the above-obtained Compound (IV) is heated at temperatures of 90° to 110° C. in an aqueous solution of acetic acid with a concentration of 50 to 90 wt. %. This reaction is completed in 1 to 20 hours. After the completion of the reaction, the solvent is distilled away from the reaction solution, so that Compound (V) is obtained in the form of a crude product.

In Reaction Formula 3, the Compound (V) is allowed to react with an equimolar amount of an indolium derivative [Compound (VI-a)] or an indoline [Compound (VI-b)]. When the Compound (V) is allowed to react with an equimolar amount of the indolium derivative [Compound (VI-a)], the reaction is carried out in the presence of an equimolar amount of quinoline at 90° to 100° C. This reaction is completed in 1 to 5 hours. As the solvent used in Reaction Formula 3, alcohol-based solvents having 4 to 8 carbon atoms may be used alone or mixed solvents of the above alcohol-based solvents in an amount of 50 vol % or more and benzene or toluene may be used.

After the completion of the reaction, the solvent is distilled away from the reaction mixture and the residue is subjected to column chromatography using a silica gel. Thus, Compound (I), the squarylium compound of the present invention, can be isolated.

Specific examples of the squarylium compounds according to the present invention are listed in Table 1.

substrate and the recording layer, or a protective layer may be formed on the recording layer.

Furthermore, an optical information recording medium with an air-sandwich structure can be obtained by disposing a pair of optical information recording media with the above-mentioned structure in a concentric configuration. Two recording media are sealed via an air space interposed therebetween, with the respective recording layers turned inside. Alternatively, one optical information recording medium having the above-mentioned structure may be sealed with the other recording medium with the same structure as the above, with a protective layer interposed therebetween and the respective recording layers turned inside, to form an optical information recording medium with a sealed-type structure.

The present invention will now be explained by referring to the materials which constitute the optical information recording medium according to the present invention, and the requirements of each layer.

(1) Substrate

Only when the laser beam is applied to the substrate

TABLE 1

| No. | $R^1$ | $R^2$ | n | $R^3$ | p | $R^4$ | $R^5$ | $R^6$ | $R^7$ | q | $R^8$ |
|---|---|---|---|---|---|---|---|---|---|---|---|
| 1 | Me | Me | 0 | | 1 | 3-NMe$_2$ | Me | Me | Me | 0 | |
| 2 | Me | Me | 0 | | 1 | 3-NMe$_2$ | Me | Me | Me | 2 | 1-A-2 |
| 3 | Me | Me | 0 | | 1 | 3-NMe$_2$ | Me | Me | Ph | 0 | |
| 4 | Me | Me | 0 | | 1 | 3-OMe | Me | Me | Me | 2 | 1-A-2 |
| 5 | Me | Me | 0 | | 1 | 3-OMe | Me | Me | Ph | 0 | |
| 6 | Bz | Bz | 0 | | 1 | 3-NMe$_2$ | Me | Me | Me | 2 | 1-A-2 |
| 7 | Me | Me | 1 | 1-Me | 2 | 3-NMe$_2$ 1-Me | Me | Me | Me | 2 | 1-A-2 |
| 8 | Et | Et | 1 | 1-Me | 2 | 3-NEt$_2$ 1-Cl | Me | Me | Me | 2 | 1-A-2 |
| 9 | Me | Me | 1 | 1-OH | 0 | | Me | Me | Me | 2 | 1-A-2 |
| 10 | Me | Me | 0 | | 2 | 1-Cl 3-Cl | Me | Me | Me | 2 | 1-A-2 |
| 11 | Me | Me | 1 | 1-OMe | 2 | 1-OMe 3-NMe$_2$ | Me | Me | Me | 2 | 1-A-2 |
| 12 | Et | Ph | 0 | | 1 | 3-NEt(Ph) | Me | Me | Me | 2 | 1-A-2 |
| 13 | Me | Me | 0 | | 2 | 1-Me 3-OMe | Me | Me | Me | 2 | 1-A-2 |
| 14 | Me | Me | 0 | | 0 | | Me | Me | Me | 0 | |
| 15 | Me | Me | 0 | | 1 | 3-Me | Me | Me | Me | 0 | |
| 16 | Me | Me | 0 | | 1 | 3-Cl | Me | Me | Me | 0 | |

In the above table, the following symbols respectively denote as follows:

Me ... Methyl group
Et ... Ethyl group
Ph ... Phenyl group
A ... —CH=CH—CH=CH—
Bz ... Benzyl group In the table, the numbers prefixed to the substituents denote the substitution positions thereof.

Compounds No. 1 to No. 5 and No. 14 to No. 16 listed in Table 1 are prepared in Synthesis Examples 1 to 8 to be described later.

As previously mentioned, the squarylium compounds according to the present invention are appropriate as the recording materials for an optical information recording medium.

The optical information recording medium according to the present invention is basically constructed in such a fashion that a recording layer comprising the squarylium compound of formula (I) is overlaid on a substrate. When necessary, an intermediate layer such as an undercoat layer may be interposed between the side to perform the recording and reproducing operation, the substrate of the optical information recording medium is required to be transparent. It is unnecessary to make the substrate transparent when the laser beam is applied to the recording layer side for the recording and reproducing operation.

Examples of the materials for the substrate are plastics such as polyester, acrylic resin, polyamide resin, polycarbonate resin, polyolefin resin, phenolic resin, epoxy resin and polyimide resin; glass; ceramics; and metals.

The preformats for address signals and pregrooves (very fine grooves for guiding information) may be formed on the surface of the substrate.

(2) Recording layer

Information is recorded in the recording layer by some optical changes of the layer, which may be caused when the recording layer is exposed to laser beams. The recording layer for use in the present invention comprises as the main component the squarylium compound of formula (I). The squarylium compounds Nos. 1 to 16 in Table 1 are preferable examples of the recording material for use in the recording layer of the recording medium of the present invention.

To improve the recording characteristics and stability of the recording layer, dyes such as polymethine dyes, phthalocyanine dyes, tetrahydrocholine dyes, dioxazine dyes, triphenothiazine dyes, phenanthrene dyes, anthraquinone (indanthrene) dyes, cyanine (merocyanine) dyes, croconium dyes, xanthene dyes, triarylmethane dyes, pyrylium dyes, indophenol dyes and azulene dyes; and metals and metallic compounds such as In, Sn, Te, Bi, Al, Se, $TeO_2$, $SnO_2$, As and Cd may be dispersed in the recording layer. Alternatively, the above dyes, metals and metallic compounds may be laminated on the recording layer.

In the recording layer, high polymeric materials or low molecular compounds which are capable of absorbing light having a longer wavelength than that of the light that can be absorbed by the squarylium compound of the present invention may be dispersed. Examples of the above low molecular compounds include organic compounds, such as an aminium compound, an imonium compound and a diimonium compound; and inorganic complex compounds, such as a bisdithiodiketone complex and a bisphenyldithiol complex.

The recording layer may further contain a preservability stabilizing agent such as metal complexes and phenolic compounds; a dispersant, a flame retardant, a lubricant and a plasticizer.

It is preferable that the thickness of the recording layer be in the range of 100Å to 10 μm, and more preferably in the range of 200Å to 2 μm.

The recording layer can be formed on the substrate by the conventional methods, such as deposition, chemical vapor deposition (CVD), sputtering and solution coating. In particular, when the solution coating method is used, dip coating, spray coating, spinner coating, blade coating, roller coating and curtain coating ar available.

(3) Undercoat layer

The undercoat layer is formed between the substrate and the recording layer for the following purposes: (a) improving the adhesion strength between the substrate and the recording layer; (b) preventing the recording layer from the exposure to water and gas; (c) improving the preservation stability of the recording layer; (d) increasing the reflectance of the recording layer; (e) protecting the substrate from the solvent employed; and (f) forming the pregrooves thereon.

To attain the above-mentioned purpose (a), a variety of polymeric materials such as ionomer resins, polyamide resins, vinyl resins, natural resins, natural polymeric materials, silicone and liquid rubber; and a silane coupling agent may be used.

To attain the purposes (b) and (c), inorganic compounds such as $BiO_2$, $MgF_2$, SiO, $TiO_2$, ZnO, TiN and SiN; and metals and metalloids such as Zn, Cu, S, Ni, Cr, Ge, Se, Au, Ag and As can be used in addition to the above-mentioned polymeric materials.

To attain the purpose (d), metals such as Al, Ag and Te can be used. An organic thin film showing a metallic luster which comprises methine dyes and xanthene dyes can be used as the undercoat layer.

To attain the purposes (e) and (f), an ultraviolet-curing resin, a thermosetting resin and a thermoplastic resin can be used in the undercoat layer.

(4) Protective Layer

The protective layer is formed on the recording layer to protect the recording layer from taking scratches, and prevent the dust and stain from directly adhering to the recording layer. In addition, the protective layer is also provided with the aim of the improvement in preservation stability and reflectance of the recording layer.

The same materials as used in the preparation of the undercoat layer can be employed for the protective layer.

In the undercoat layer and the protective layer, a stabilizer, a dispersant, a flame-retardant, a lubricant, an antistatic agent, a surface active agent and a plasticizer may be contained. Furthermore, the undercoat layer and the protective layer may comprise the squarylium compound of formula (I) according to the present invention.

As previously explained, the squarylium compounds of formula (I) according to the present invention are readily vacuum-deposited. In addition, the squarylium compounds of formula (I) have high solubility in organic solvents, so that they can be subjected to solution coating; and show excellent compatibility with high polymeric materials and improved preservation stability.

By using such squarylium compounds of formula (I) as recording materials, optical information recording media having high reflectance and improved preservation and reproduction stabilities, and capable of recording images with high contrast can be produced.

Other features of this invention will become apparent in the course of the following description of exemplary embodiments, which are given for illustration of the invention and ar not intended to be limiting thereof.

SYNTHESIS EXAMPLE 1

Preparation of Squarylium Compounds No. 1

To a mixture of 75 ml of dichloromethane and 1.5 g of 3,4-dichloro-3-cyclobutene-1,2-dione, 2.7 g of 1,1-bis(p-dimethylaminophenyl)ethylene was added at room temperature.

After one-hour stirring, the dichloromethane was distilled away from the reaction solution by a rotary evaporator. To the thus obtained residue, 38 ml of acetic acid and 10 ml of water were added, and the mixture was heated on an oil bath at 100° C. for 1 hour.

Thereafter the acetic acid and the water were distilled away from the reaction mixture by the rotary evaporator. To the thus obtained residue, 98 ml of n-butanol and 1.73 g of 1,3,3-trimethyl-2-methylene indoline were added and the mixture was heated on the oil bath at 100° C. for 1 hour.

After the completion of the reaction, the solvent and the water generated in the course of the reaction were distilled away from the reaction mixture. The residual product was purified by column chromatography, so that 1.6 g of squarylium compound No. 1 according to the present invention was obtained.

The melting point of the squarylium compound No. 1 was 210°-to 216° C.

The results of the elemental analysis of the thus obtained product were as follows:

|  | % C | % H | % N |
| --- | --- | --- | --- |
| Calculated | 78.89 | 6.82 | 8.12 |

| | % C | % H | % N |
|---|---|---|---|
| Found | 78.70 | 6.80 | 8.20 |

The above calculation was based on the formula for the sequarylium compound No. 1 of $C_{34}H_{35}N_3O_2$.

Figure 1:
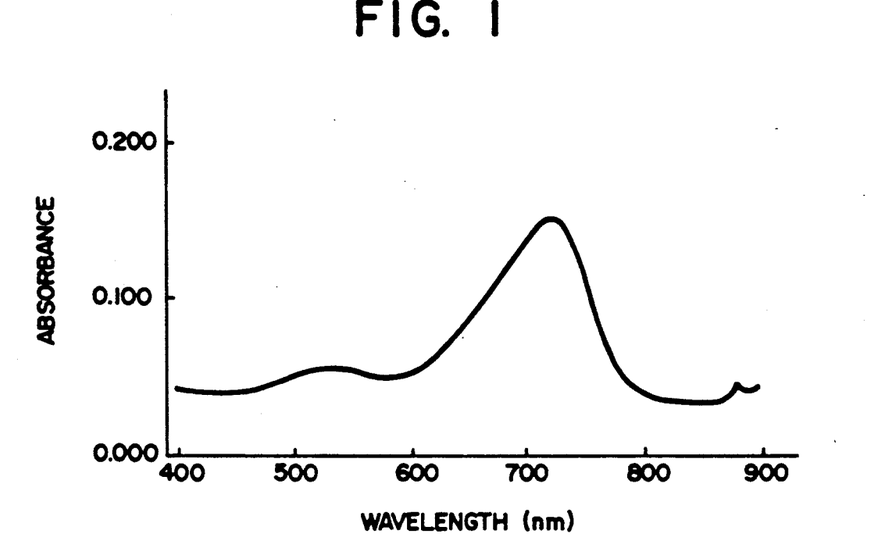
FIGS. 1 to 8 are spectroscopic characteristic charts of squarylium compounds according to the present invention, which are obtained in Synthesis Examples, 5

A spectroscopic characteristic chart of this compound is shown in FIG. 1 ($\lambda_{max}$: 721 nm, log$\epsilon$: 4.9, solvent: $CHCl_3$).

SYNTHESIS EXAMPLE 2

Preparation of Squarylium Compound No. 2

To a mixture of 75 ml of dichloromethane and 1.5 g of 3,4-dichloro-3-cyclobutene-1,2-dione, 2.7 g of 1,1-bis(p-dimethylaminophenyl)ethylene was added at room temperature.

After one-hour stirring, the dichloromethane was distilled away from the reaction solution by a rotary evaporator. To the thus obtained residue, 38 ml of acetic acid and 10 ml of water were added, and the mixture was heated on an oil bath at 100° C. for 1 hour.

Thereafter the acetic acid and the water were distilled away from the reaction mixture by the rotary evaporator. To the thus obtained residue, 98 ml of n-butanol, 50 ml of toluene, 3.5 g of 1,1,2,3-tetramethylbenz[e]indolium iodide and 1.3 g of qinoline were added and the mixture was heated on the oil bath at 100° C. for 1 hour.

After the completion of the reaction, the reaction mixture was cooled and then concentrated by distilling the solvent away therefrom by the rotary evaporator. The residual product was purified by column chromatography, so that 1.6 g of squarylium compound No. 2 according to the present invention was obtained.

The melting point of the squarylium compound No. 2 was 177° to 180° C.

The results of the elemental analysis of the thus obtained product were as follows:

| | % C | % H | % N |
|---|---|---|---|
| Calculated | 80.39 | 6.57 | 7.40 |
| Found | 80.48 | 6.69 | 7.31 |

The above calculation was based on the formula for the squarylium compound No. 2 of $C_{38}H_{37}N_3O_2$.

Figure 2:
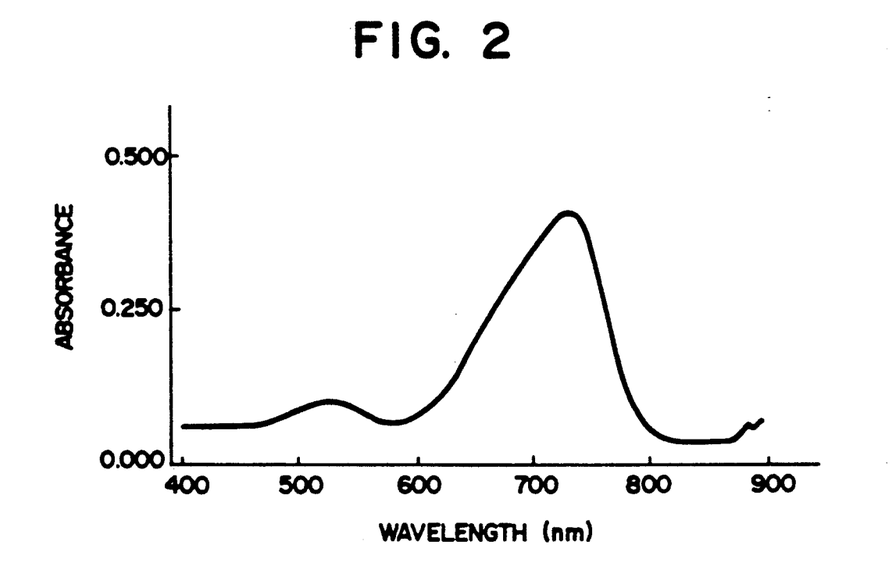

A spectroscopic characteristic chart of this compound is shown in FIG. 2 ($\lambda_{max}$: 732 nm, log$\epsilon$: 4.9, solvent: $CHCl_3$).

SYNTHESIS EXAMPLE 3

Preparation of Squarylium Compound No. 3

The procedure for preparation of squarylium compound No. 1 in Synthesis Example 1 was repeated except that 1.73 g of 1,3,3-trimethyl-2-methylene indoline was replaced by 2.4 g of 3,3-dimethyl-2-methylene-1-phenyl indoline, so that 1.8 g of squarylium compound No. 3 according to the present invention was obtained.

The melting point of the squarylium compound No. 3 was 245° to 250° C.

The results of the elemental analysis of the thus obtained product were as follows:

| | % C | % H | % N |
|---|---|---|---|
| Calculated | 80.39 | 6.57 | 7.40 |
| Found | 80.48 | 6.69 | 7.31 |

The above calculation was based on the formula for the squarylium compound No. 3 of $C_{38}H_{37}N_3O_2$.

Figure 3:
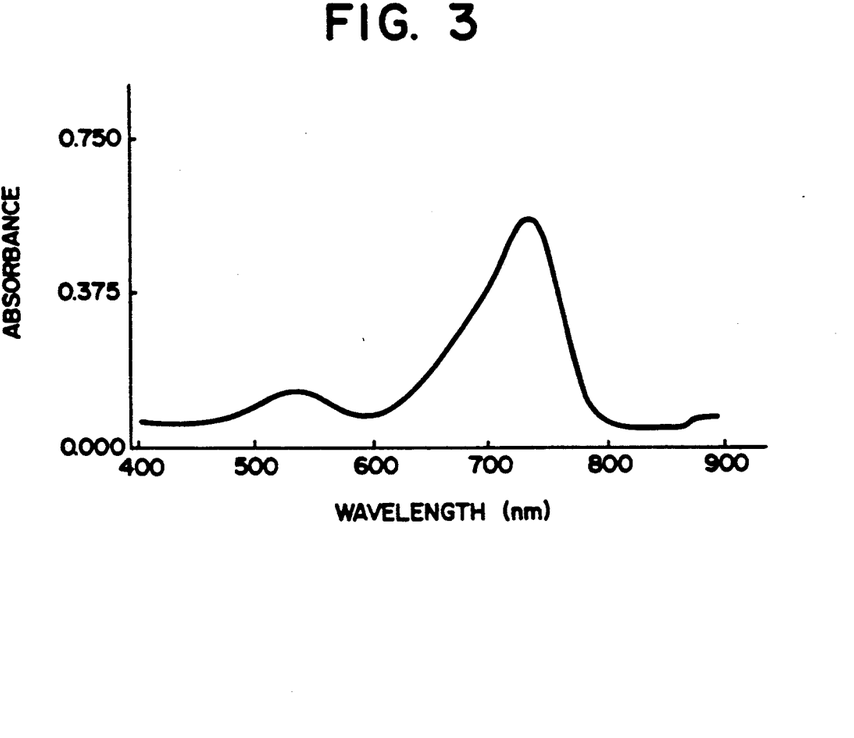

A spectroscopic characteristic chart of this compound shown in FIG. 3 ($\lambda_{max}$: 740 nm, log$\epsilon$: 5.0, solvent: $CHCl_3$).

SYNTHESIS EXAMPLE 4

Preparation of Squarylium Compound No. 4

The procedure for preparation of squarylium compound No. 2 in Synthesis Example 2 was repeated except that 2.7 g of 1,1-bis(p-dimethylaminophenyl)ethylene was replaced by 2.5 g of 1-(p-dimethylaminophenyl)-1-(p-methoxyphenyl) ethylene, so that 1.0 g of squarylium compound No. 4 according to the present invention was obtained.

The melting point of the squarylium compound No. 4 was 182° to 185° C.

The results of the elemental analysis of the thus obtained product were as follows:

| | % C | % H | % N |
|---|---|---|---|
| Calculated | 80.12 | 6.18 | 5.05 |
| Found | 79.95 | 6.32 | 5.24 |

The above calculation was based on the formula for the squarylium compound No. 4 of $C_{37}H_{34}N_2O_3$.

Figure 4:
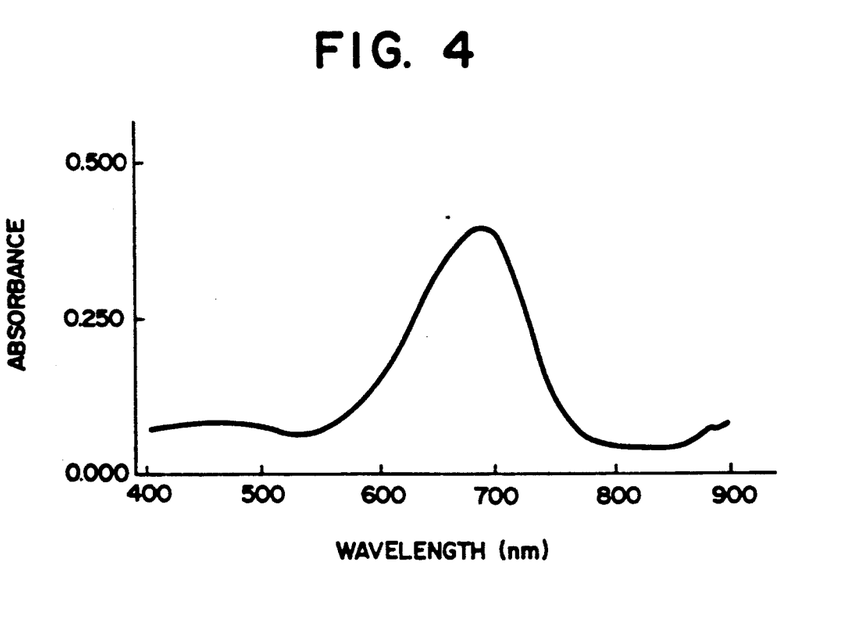

A spectroscopic characteristic chart of this compound is shown in FIG. 4 ($\lambda_{max}$: 690 nm, log$\epsilon$: 4.9, solvent: $CHCl_3$).

SYNTHESIS EXAMPLE 5

Preparation of Squarylium Compound No. 5

The procedure for preparation of squarylium compound No. 3 in Synthesis Example 3 was repeated except that 2.7 g of 1,1-bis(p-dimethylaminophenyl)ethylene was replaced by 2.5 g of 1-(p-dimethylaminophenyl)-1-(p-methoxyphenyl) ethylene, so that 1.1 g of squarylium compound No. 5 according to the present invention was obtained.

The melting point of the squarylium compound No. 5 was 195° to 200° C.

The results of the elemental analysis of the thus obtained product were as follows:

| | % C | % H | % N |
|---|---|---|---|
| Calculated | 80.54 | 6.05 | 4.94 |
| Found | 80.34 | 6.11 | 4.87 |

The above calculation was based on the formula for the squarylium compound No. 5 of $C_{38}H_{34}N_2O_3$.

Figure 5:
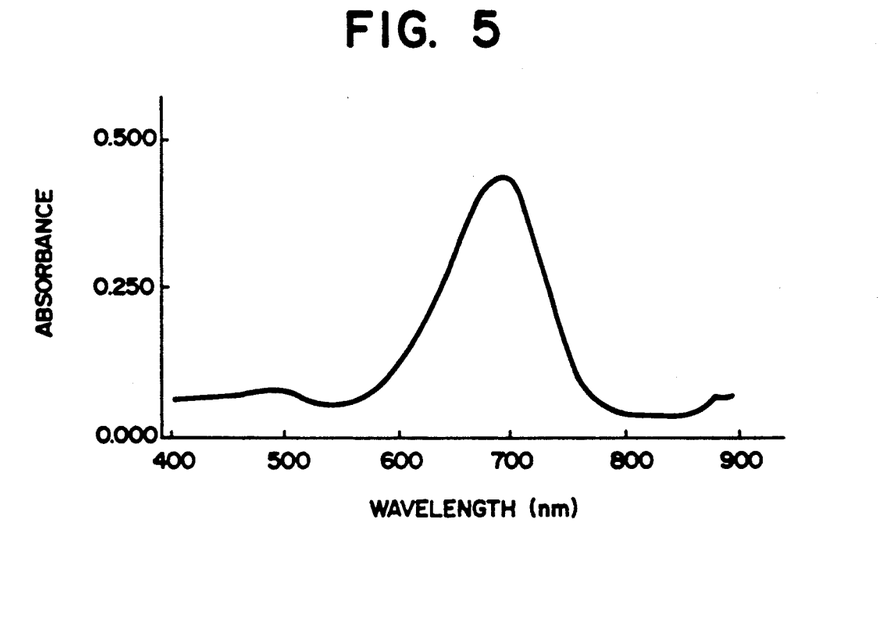

A spectroscopic characteristic chart of this compound is shown in FIG. 5 ($\lambda_{max}$: 698 nm, log$\epsilon$: 4.9, solvent: $CHCl_3$).

SYNTHESIS EXAMPLE 6

Preparation of Squarylium Compound No. 14

The procedure for preparation of squarylium compound No. 1 in Synthesis Example 1 was repeated except that 2.7 g of 1,1-bis(p-dimethylaminophenyl)ethylene was replaced by 2.2 g of 1-(p-dimethylaminophenyl)-1-phenyl ethylene, so that 1 g of squarylium compound No. 14 according to the present invention was obtained.

The melting point of the squarylium compound No. 14 was 148° to 152.5° C.

The results of the elemental analysis of the thus obtained product were as follows:

|  | % C | % H | % N |
|---|---|---|---|
| Calculated | 80.98 | 6.37 | 5.90 |
| Found | 80.70 | 6.55 | 5.79 |

The above calculation was based on the formula for the squarylium compound No. 14 of $C_{32}H_{30}N_2O_2$. squarylium compound No. 14 of $C_{32}H_{30}HN_{22}$.

Figure 6:
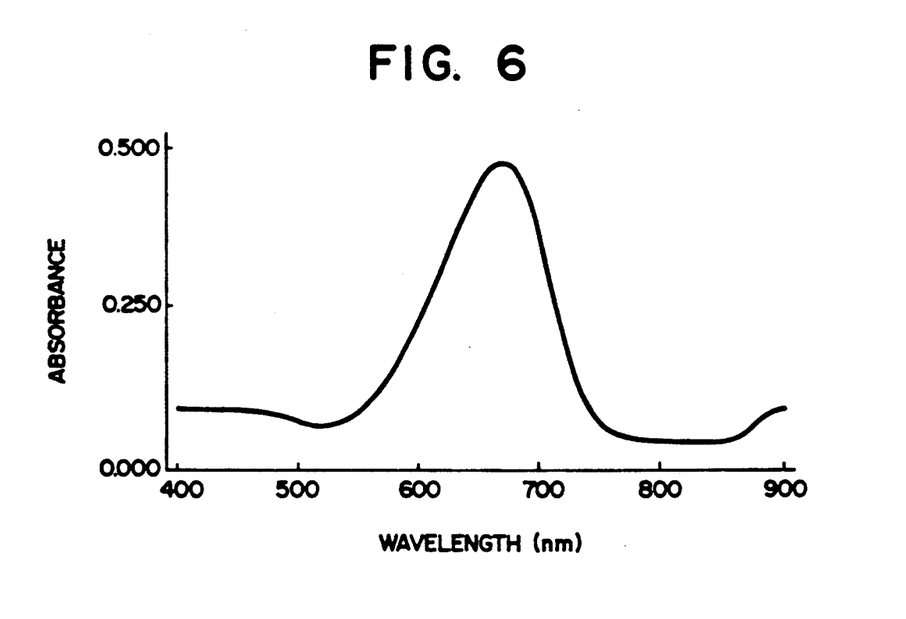

A spectroscopic characteristic chart of this compound is shown in FIG. 6 ($\lambda_{max}$: 670nm, log$\epsilon$: 4.9, solvent: $CHCl_3$).

SYNTHESIS EXAMPLE 7

Preparation of Squarylium Compound No. 15

The procedure for preparation of squarylium compound No. 1 in Synthesis Example 1 was repeated except that 2.7 g of 1,1-bis(p-dimethylaminophenyl)ethylene was replaced by 2.4 g of 1-(p-dimethylaminophenyl)-1-(p-methylphenyl) ethylene, so that 1.2 g of squarylium compound No. 15 according to the present invention was obtained.

The melting point of the squarylium compound No. 15 was 155.5° to 157.0° C.

The results of the elemental analysis of the thus obtained product were as follows:

|  | % C | % H | % N |
|---|---|---|---|
| Calculated | 81.12 | 6.60 | 5.73 |
| Found | 81.41 | 6.37 | 5.55 |

The above calculation was based on the formula for the squarylium compound No. 15 of $C_{33}H_{32}N_2O_2$.

Figure 7:
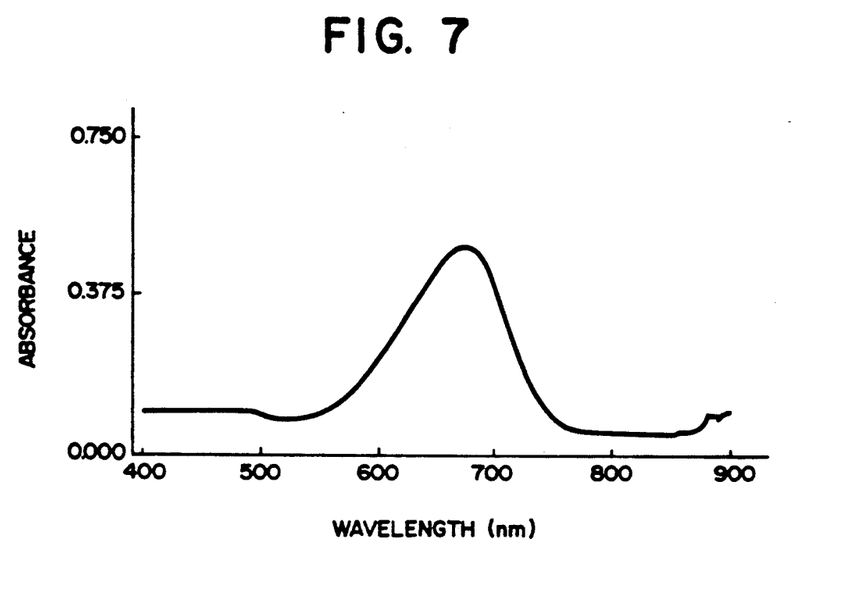

A spectroscopic characteristic chart of this compound is shown in FIG. 7 ($\lambda_{max}$: 674 nm, log$\epsilon$: 4.9, solvent: $CHCl_3$).

SYNTHESIS EXAMPLE 8

Preparation of Squarylium Compound No. 16

The procedure for preparation of squarylium compound No. 1 in Synthesis Example 1 was repeated except that 2.7 g of 1,1-bis(p-dimethylaminophenyl)ethylene was replaced by 2.6 g of 1-(p-dimethylaminophenyl)-1-(p-chlorophenyl) ethylene, so that 0.6 g of squarylium compound No. 16 according to the present invention was obtained.

The melting point of the squarylium compound No. 16 was 156.0° to 159.0° C.

The results of the elemental analysis of the thus obtained product were as follows:

|  | % C | % H | % N |
|---|---|---|---|
| Calculated | 75.50 | 5.74 | 5.50 |
| Found | 75.46 | 5.48 | 5.32 |

The above calculation was based on the formula for the squarylium compound No. 16 of $C_{32}H_{29}ClN_2O_2$.

Figure 8:
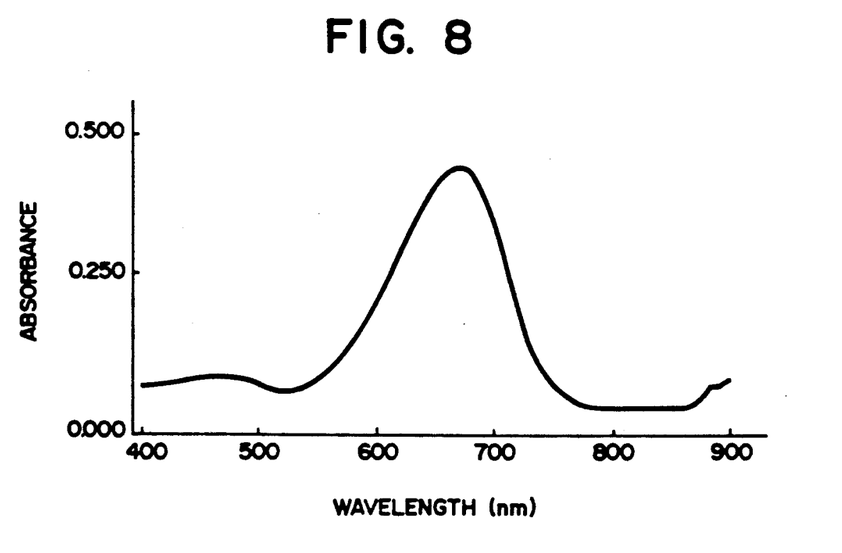

A spectroscopic characteristic chart of this compound is shown in FIG. 8 ($\lambda_{max}$: 670 nm, log$\epsilon$: 4.8, solvent: $CHCl_3$).

EXAMPLE 1

On an acrylic photopolymer with a thickness of 50 μm formed on a polymethyl methacrylate disk having a thickness of 1.2 mm and a diameter of 130 mm, a spiral guide groove with a pitch of 1.6 μm, a depth of 2000Å and a half width of 0.4 μm was formed, whereby a substrate was prepared.

A 0.8 wt. % 1,2-dichloroethane solution of the squarylium compound No. 2 obtained in Synthesis Example 2 was spin-coated on the above-prepared substrate and dried, so that a recording layer having a thickness of about 800Å was formed on the substrate. Thus, optical information recording medium No. 1 according to the present invention was prepared.

Figure 9:
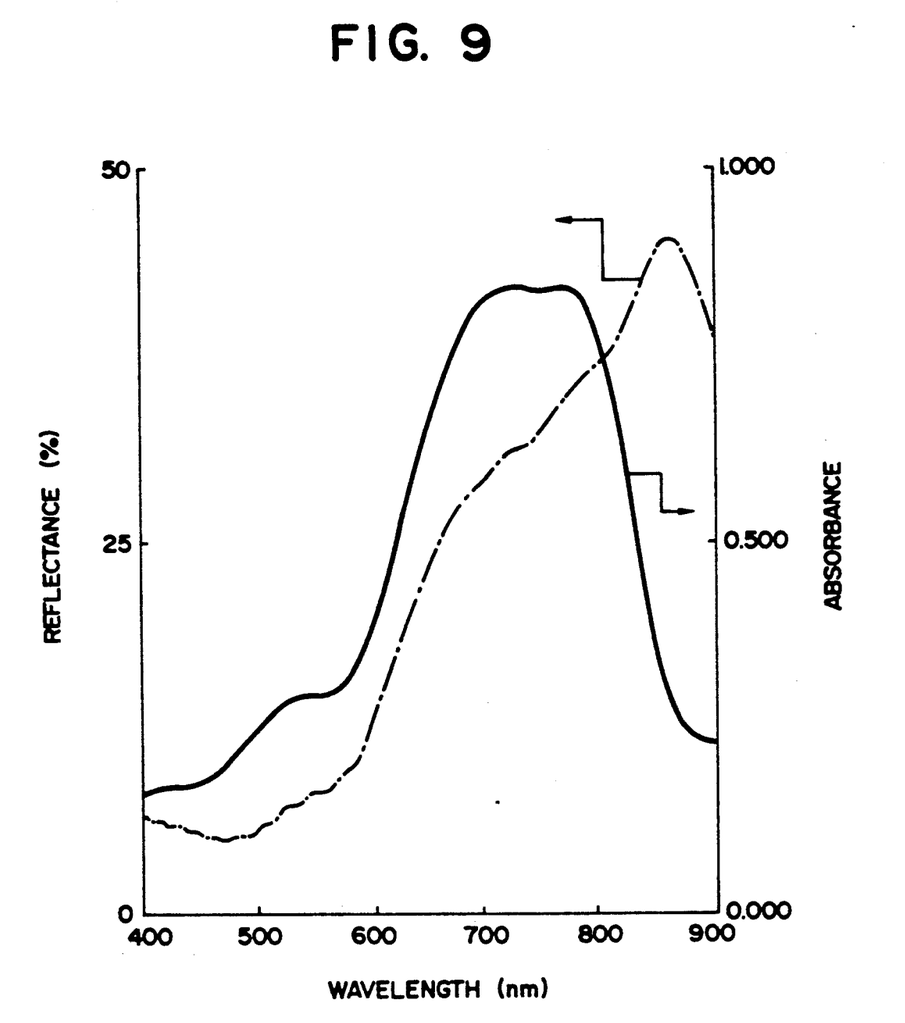
FIGS. 9 to 11 are charts showing the reflection and absorption curves of optical information recording media No. 1, No. 2 and No. 5 according to the present invention, which are obtained in Examples 1, 2 and 5, respectively.

FIG. 9 shows a spectroscopic characteristic chart of the thus prepared optical information recording medium No. 1, which was obtained by applying parallel light beams to a smooth portion of the substrate of the above-prepared recording medium No. 1.

As can be seen from the chart in FIG. 9, the optical information recording medium No. 1 shows high reflectance in a region of 780 to 830 nm, which corresponds to the wavelength range of semiconductor laser beams, which are currently used for the optical disks.

To evaluate the recording characteristics of the above-prepared optical information recording medium No. 1, information was recorded by applying a semiconductor laser beam having a beam diameter of 1.6 μm and a wavelength of 790 nm to the substrate side of the recording medium No. 1, under the conditions of a recording frequency of 1.25 MHz, a line speed of 2.1 m/sec, and a recording power of 3 mW.

Using the same semiconductor laser as in the above, a laser beam having an intensity of 0.2 $mW/cm^2$ was applied to the recording medium to reproduce the recorded information and the light reflected from the recording medium was detected. The detected light was subjected to a spectral analysis, using a scanning filter at a band width of 30 kHz, so that the initial C/N (Carrier/Noise) ratio was obtained.

Further, the reflectance (initial value) at the land portion of the guide groove was also measured by using the same semiconductor laser beams.

The results are shown in Table 2.

In addition to the above, the stability of the optical information recording medium No. 1 to the reproduction light was evaluated by conducting a reproduction deterioration acceleration test. In this test, the recording medium No. 1 was exposed to tungsten light of 80,000 lux for 10 hours. After the irradiation, the reflectance and the C/N ratio of the recording medium were measured in the same manner as in the above. The results of this acceleration test are also shown in Table 2.

Furthermore, to evaluate the preservation stability of the optical information recording medium No. 1, the recording medium was allowed to stand at 60° C. and 90% RH for 2,000 hours. Then, the reflectance and the C/N ratio of the recording medium were measured in the same manner as in the above. The results are also shown in Table 2.

EXAMPLE 2

The procedure for preparation of the optical information recording medium No. 1 in Example 1 was repeated except that the squarylium compound No. 2 used as the recording material in Example 1 was replaced by squarylium compound No. 1 prepared in Synthesis Example 1, whereby optical information recording medium No. 2 according to the present invention was prepared.

Figure 10:
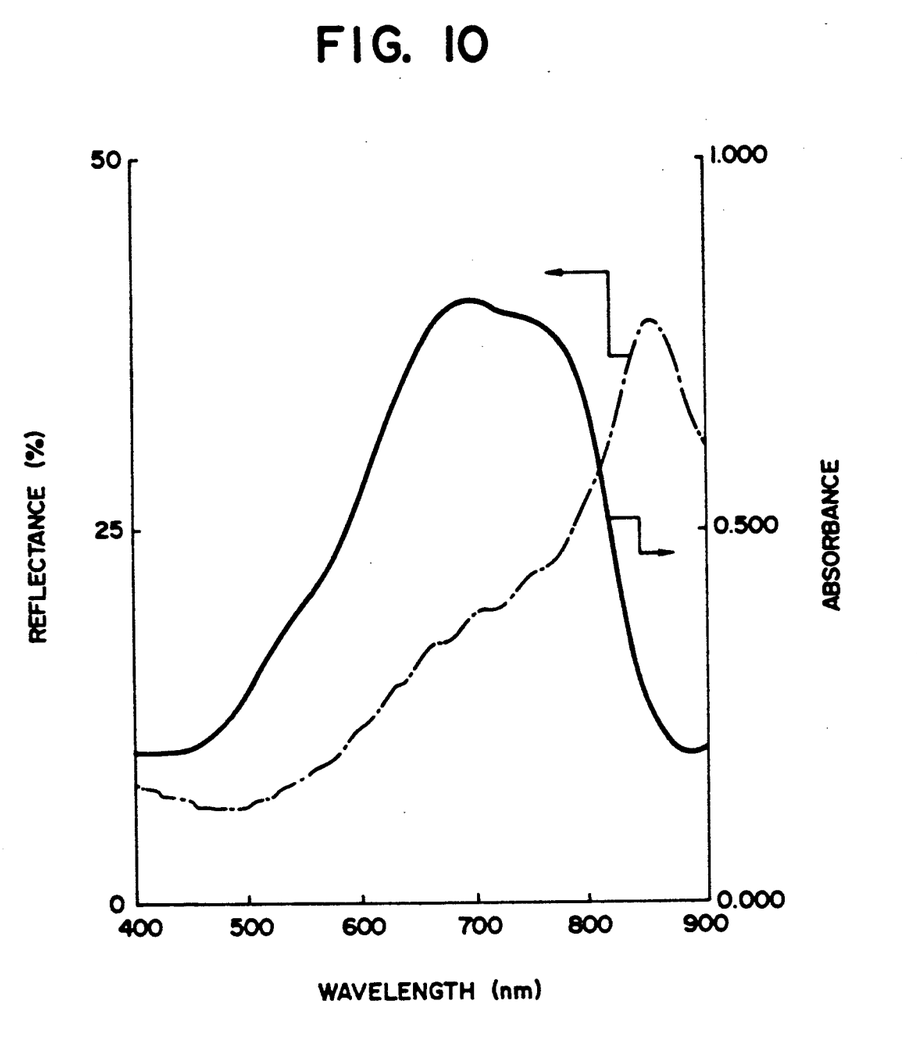

FIG. 10 shows a spectroscopic characteristic chart of the thus prepared recording medium No. 2, obtained in the same manner as in Example 1.

The recording characteristics of the recording medium No. 2 were evaluated in the same manner as in Example 1. The results are shown in Table 2.

EXAMPLE 3

The procedure for preparation of the optical information recording medium No. 1 in Example 1 was repeated except that the squarylium compound No. 2 used as the recording material in Example 1 was replaced by squarylium compound No. 10, whereby optical information recording medium No. 3 according to the present invention was prepared.

The recording characteristics of the recording medium No. 3 were evaluated in the same manner as in Example 1. The results are shown in Table 2.

EXAMPLE 4

The procedure for preparation of the optical information recording medium No. 1 in Example 1 was repeated except that the squarylium compound No. 2 used as the recording material in Example 1 was replaced by squarylium compound No. 11, whereby optical information recording medium No. 4 according to the present invention was prepared.

The recording characteristics of the recording medium No. 4 were evaluated in the same manner as in Example 1. The results are shown in Table 2.

EXAMPLE 5

An injection-molded polycarbonate disk having a thickness of 1.2 mm and a diameter of 130 mm, with the same guide grooves as in Example 1, formed by using a stamper capable of transferring a groove pattern identical to the guide grooves in Example 1, was spin-coated with a 1 wt. % methanol - 1,2-dichloroethane - butanol solution (weight ratio=8/2/0.5) of squarylium compound No. 3 prepared in Synthesis Example 3, so that a recording layer was formed on the substrate. Thus, optical information recording medium No. 5 according to the present invention was prepared.

Figure 11:
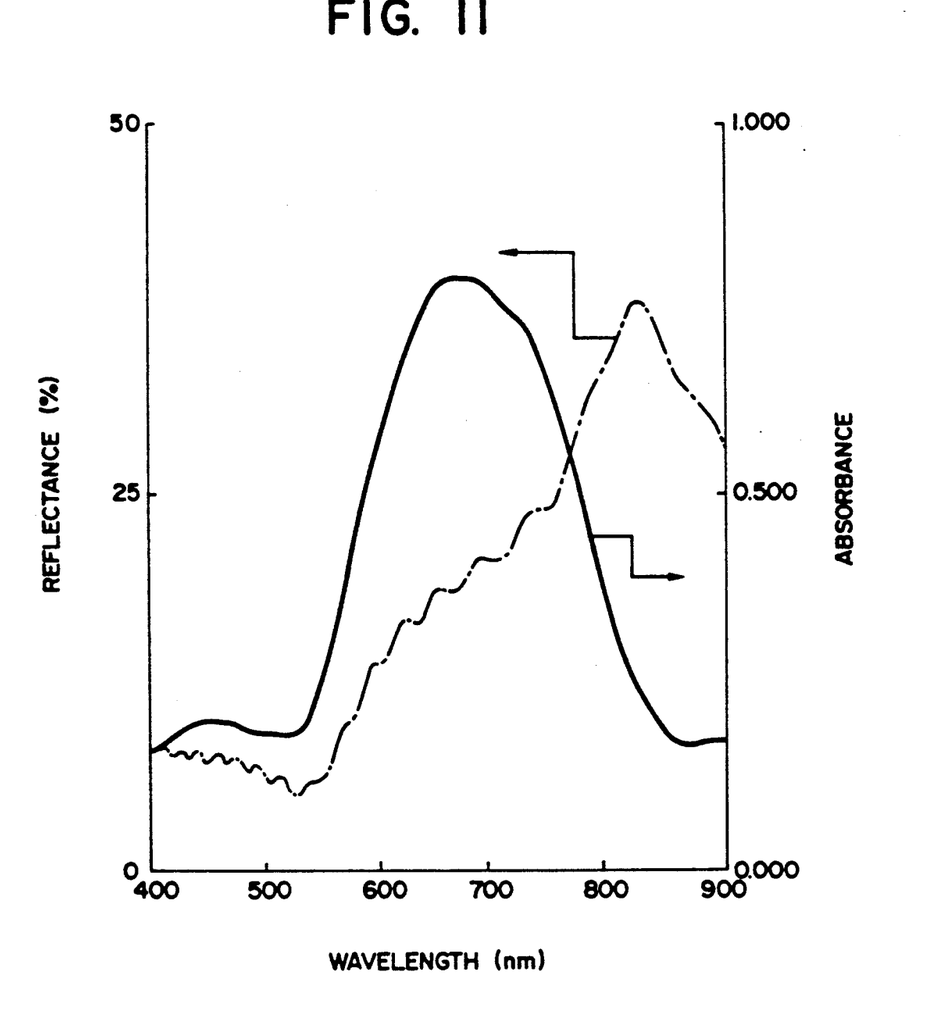

FIG. 11 is a spectroscopic chart of the recording medium No. 5.

The recording characteristics of the recording medium No. 5 were evaluated in the same manner as in Example 1. The results are shown in Table 2.

EXAMPLE 6

The procedure for preparation of the optical information recording medium No. 5 in Example 5 was repeated except that the squarylium compound No. 3 used as the recording material in Example 5 was replaced by squarylium compound No. 4 prepared in Synthesis Example 4, whereby optical information recording medium No. 6 according to the present invention was prepared.

The recording characteristics of the recording medium No. 6 were evaluated in the same manner as in Example 1. The results are shown in Table 2.

EXAMPLE 7

The procedure for preparation of the optical information recording medium No. 5 in Example 5 was repeated except that the squarylium compound No. 3 used as the recording material in Example 5 was replaced by squarylium compound No. 5 prepared in Synthesis Example 5, whereby optical information recording medium No. 7 according to the present invention was prepared.

The recording characteristics of the recording medium No. 7 were evaluated in the same manner as in Example 1. The results are shown in Table 2.

EXAMPLE 8

The procedure for preparation of the optical information recording medium No. 5 in Example 5 was repeated except that the squarylium compound No. 3 used as the recording material in Example 5 was replaced by squarylium compound No. 8, whereby optical information recording medium No. 8 according to the present invention was prepared.

The recording characteristics of the recording medium No. 8 were evaluated in the same manner as in Example 1. The results are shown in Table 2.

EXAMPLE 9

The procedure for preparation of the optical information recording medium No. 2 in Example 2 was repeated except that the squarylium compound No. 1 used as the recording material in Example 2 was replaced by a mixture of squarylium compound No. 1 and a compound of the following formula (A) (weight ratio =1/1), whereby optical information recording medium No. 9 according to the present invention was prepared.

The recording characteristics of the recording medium No. 9 were evaluated in the same manner as in Example 1. The results are shown in Table 2.

EXAMPLE 10

The procedure for preparation of the optical information recording medium No. 1 in Example 1 was repeated except that the squarylium compound No. 2 used as the recording material in Example 1 was replaced by a mixture of squarylium compound No. 2 and a compound of the following formula (B) (weight ratio=85/15), whereby optical information recording medium No. 10 according to the present invention was prepared.

The recording characteristics of the recording medium No. 10 were evaluated in the same manner as in Example 1. The results are shown in Table 2.

EXAMPLE 11

The procedure for preparation of the optical information recording medium No. 1 in Example 1 was repeated except that the squarylium compound No. 2 used as the recording material in Example 1 was replaced by a mixture of squarylium compound No. 2 and a compound of the following formula (C) (weight ratio=85/15), whereby optical information recording medium No. 11 according to the present invention was prepared.

(C)

The recording characteristics of the recording medium No. 11 were evaluated in the same manner as in Example 1. The results are shown in Table 2.

EXAMPLE 12

An injection-molded polycarbonate disk having a thickness of 1.2 mm and a diameter of 130 mm, with the same guide grooves as in Example 1, formed by using a stamper capable of transferring a groove pattern identical to the guide grooves in Example 1, was coated with a 25% butanol solution of "Colcoat N 103X" (Trademark), made by Colcoat Co., Ltd., and dried at 60° C. for 2 hours, so that an undercoat layer was formed on the substrate.

A 1 wt. % methanol - 1,2-dichloroethane - butanol solution (weight ratio=8/2/0.5) of squarylium compound No. 3 prepared in Synthesis Example 3 was spin-coated on the above-prepared undercoat layer, so that a recording layer was formed on the undercoat layer. Thus, optical information recording medium No. 12 according to the present invention was prepared.

The recording characteristics of the recording medium No. 12 were evaluated in the same manner as in Example 1. The results are shown in Table 2.

EXAMPLE 13

On an acrylic photopolymer with a thickness of 50 μm formed on a polymethyl methacrylate disk having a thickness of 1.2 mm and a diameter of 130 mm, a spiral guide groove with a pitch of 1.6 μm, a depth of 2000Å and a half width of 0.4 μm was formed, whereby a substrate was prepared.

A 0.8 wt. % 1,2-dichloroethane solution of the squarylium compound No. 2 obtained in Synthesis Example 2 was spin-coated on the above-prepared substrate and dried, so that a recording layer having a thickness of about 800Å was formed on the substrate.

Gold was vacuum-deposited to the above-prepared recording layer under a vacuum degree of $10^{-5}$ Torr, so that a protective layer having a thickness of 100Å was formed on the recording layer. Thus, optical information recording medium No. 13 according to the present invention wa prepared.

The recording characteristics of the recording medium No. 13 were evaluated in the same manner as in Example 1. The results arc shown in Table 2.

EXAMPLE 14

The same guide grooves as in Example 1 were formed on an injection-molded polycarbonate disk having a thickness of 1.2 mm and a diameter of 130 mm, by using a stamper capable of transferring a groove pattern identical to the guide grooves in Example 1, so that a substrate was prepared.

Tellurium was vacuum-deposited to the above-prepared substrate under a vacuum degree of $10^{-5}$ Torr, so that an undercoat layer having a thickness of 150Å was formed on the substrate.

The thus prepared undercoat layer was spin-coated with a 1 wt. % methanol - 1,2-dichloroethane - butanol solution (weight ratio =8/2/0.5) of squarylium compound No. 3 prepared in Synthesis Example 3, so that a recording layer was formed on the undercoat layer. Thus, optical information recording medium No. 14 according to the present invention was prepared.

The recording characteristics of the recording medium No. 14 were evaluated in the same manner as in Example 1. The results are shown in Table 2.

COMPARATIVE EXAMPLE 1

The procedure for preparation of the optical information recording medium No. 1 in Example 1 was repeated except that the squarylium compound No. 2 used as the recording material in Example 1 was replaced by a compound of the following formula (a), whereby comparative optical information recording medium No. 1 was prepared.

(a)

The recording characteristics of the comparative recording medium No. 1 were evaluated in the same manner as in Example 1. The results are shown in Table 2.

COMPARATIVE EXAMPLE 2

The procedure for preparation of the optical information recording medium No. 1 in Example 1 was repeated except that the squarylium compound No. 2 used as the recording material in Example 1 was replaced by a compound of the following formula (b), whereby comparative optical information recording medium No. 2 was prepared.

(b)

The recording characteristics of the comparative recording medium No. 2 were evaluated in the same manner as in Example 1. The results are shown in Table 2.

COMPARATIVE EXAMPLE 3

The procedure for preparation of the optical information recording medium No. 1 in Example 1 was repeated except that the squarylium compound No. 2 used as the recording material in Example 1 was replaced by a compound of the following formula (c), whereby comparative optical information recording medium No. 3 was prepared.

(c)

The recording characteristics of the comparative recording medium No. 3 were evaluated in the same manner as in Example 1. The results are shown in Table 2.

TABLE 2

| Recording Medium | Initial Value | | Reproduction-Deterioration Acceleration Test | | Preservation Stability Acceleration Test | |
| --- | --- | --- | --- | --- | --- | --- |
| | R(%) | C/N(dB) | R(%) | C/N(dB) | R(%) | C/N(dB) |
| No. 1 | 29 | 56 | 21 | 53 | 25 | 55 |
| No. 2 | 23 | 55 | 20 | 53 | 19.5 | 53 |
| No. 3 | 25 | 55 | 19.5 | 51 | 21.5 | 53 |
| No. 4 | 28 | 56 | 18.5 | 50 | 23 | 53 |
| No. 5 | 26 | 55 | 17.5 | 50 | 18 | 50 |
| No. 6 | 27 | 56 | 14 | 45 | 17 | 49 |
| No. 7 | 20 | 55 | 13 | 44 | 17.5 | 50 |
| No. 8 | 28 | 55 | 20.5 | 52 | 24 | 54 |
| No. 9 | 23 | 56 | 19 | 50 | 19 | 52 |
| No. 10 | 23 | 56 | 21 | 52 | 19 | 51 |
| No. 11 | 22 | 54 | 20.5 | 52 | 18.5 | 51 |
| No. 12 | 31 | 57 | 23 | 52 | 24 | 54 |
| No. 13 | 35 | 50 | 29 | 48 | 29 | 49 |
| No. 14 | 38 | 49 | 36 | 48 | 34 | 44 |
| Comp. No. 1 | 23 | 55 | 10 | — | 18 | 49 |
| Comp. No. 2 | 18 | 54 | 7 | — | 15 | 43 |
| Comp. No. 3 | 15 | 53 | 14 | 53 | * | * |

In the above table, "R" denotes the reflectance; "—" denotes that the measurement was incapable; and "*" denotes that the measurement was incapable because the recording layer was crystallized during the preservation.

What is claimed is:

1. A squarylium compound having formula (I):

in which
R[1] and R[2] independently represent hydrogen, an alkyl group having 1 to 4 carbon atoms, an aryl group which may have a substituent, or an aralkyl group having 7 to 10 carbon atoms, which may have a substituent;
R[3] represents a halogen, an alkyl group having 1 to 4 carbon atoms, an alkoxyl group having 1 to 4 carbon atoms, a nitro group, or a hydroxyl group; n is an integer of 0 to 4 and R[3]s may be the same or different when n is 2 to 4;
R[4] represents a halogen, an alkyl group having 1 to 4 carbon atoms, an alkoxyl group having 1 to 4 carbon atoms, a hydroxyl group, a nitro group, a cyano group, a trifluoromethyl group, or in which R[9] and R[10] are the same defined in R[1]; p is an integer of 0 to 5 and R[4]s may be the same or different when P is 2 to 5;
R[5] and R[6] independently represent an alkyl group having 1 to 4 carbon atoms;
R[7] represents an alkyl group having 1 to 4 carbon atoms, an aryl group which may have a substituent, or an aralkyl group having 7 to 10 carbon atoms, which may have a substituent;
R[8] represents a halogen, an alkyl group having 1 to 4 carbon atoms, an alkoxyl group having 1 to 4 carbon atoms, an aryl group which may have a substituent, or an aralkyl group having 7 to 10 carbon atoms, which may have a substituent; and q is an integer of 0 to 4 and when q is 2 to 4, R[8]s may be the same or different and form an aromatic ring which may have a substituent, in combination with two adjacent carbon atoms in the ring to which R[8]s are bonded,
wherein said substituent of said aryl group and said aralkyl group represented by R[1], R[2], R[7], R[8], R[9] and R[10] is selected from the group consisting of halogen, an alkyl group having 1 to 4 carbon atoms, and an alkoxyl group having 1 to 4 carbon atoms.

2. The squarylium compound as claimed in claim 1, wherein said alkyl group having 1 to 4 carbon atoms, represented by R[1], R[2], R[3], R[4], R[5], R[6], R[7], R[8], R[9] or R[10], is selected from the group consisting of a methyl group, an ethyl group, a propyl group, an isopropyl group, a butyl group, an isobutyl group, a sec-butyl group and a tert-butyl group.

3. The squarylium compound as claimed in claim 1, wherein said alkoxyl group having 1 to 4 carbon atoms, represented by $R^3$, $R^4$ or $R^8$, is selected from the group consisting of a methoxy group, an ethoxy group, a propoxy group and a butoxy group.

4. The squarylium compound as claimed in claim 1, wherein said halogen represented by $R^3$, $R^4$ or $R^8$ is selected from the group consisting of chlorine, bromine and fluorine.

5. The squarylium compound as claimed in claim 1, wherein said aryl group represented by $R^1$, $R^2$, $R^7$, $R^8$, $R^9$ or $R^{10}$ is selected from the group consisting of a phenyl group and a naphthyl group.

6. The squarylium compound as claimed in claim 1, wherein said aralkyl group having 7 to 10 carbon atoms, represented by $R^1$, $R^2$, $R^7$, $R^8$, $R^9$ or $R^{10}$, is selected from the group consisting of a benzyl group, a phenylethyl group and a phenylpropyl group.

7. The squarylium compound as claimed in claim 1, wherein said aromatic ring formed by $R^8$s is a benzene ring.

8. The squarylium compound as claimed in claim 1, wherein said substituent of said aromatic ring formed by $R^8$s is selected from the group consisting of a halogen, an alkyl group having 1 to 4 carbon atoms, an alkoxyl group having 1 to 4 carbon atoms, an aralkyl group having 7 to 10 carbon atoms, and an aryl group.

* * * * *